United States Patent
Aalders et al.

(10) Patent No.: US 11,433,165 B2
(45) Date of Patent: Sep. 6, 2022

(54) BREAST PUMP

(71) Applicant: KONINKLIJKE PHILIPS N.V., Eindhoven (NL)

(72) Inventors: Arnold Aalders, Waalwijk (NL); Michiel Dirk Augustinus Bijloo, Udenhout (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 317 days.

(21) Appl. No.: 14/429,115

(22) PCT Filed: Sep. 9, 2013

(86) PCT No.: PCT/IB2013/058396
§ 371 (c)(1),
(2) Date: Mar. 18, 2015

(87) PCT Pub. No.: WO2014/045159
PCT Pub. Date: Mar. 27, 2014

(65) Prior Publication Data
US 2015/0238669 A1    Aug. 27, 2015

Related U.S. Application Data

(60) Provisional application No. 61/704,700, filed on Sep. 24, 2012.

(30) Foreign Application Priority Data

Sep. 24, 2012 (EP) ..................... 12185596

(51) Int. Cl.
A61M 1/06 (2006.01)
A61M 1/00 (2006.01)

(52) U.S. Cl.
CPC ............... *A61M 1/06* (2013.01); *A61M 1/82* (2021.05)

(58) Field of Classification Search
CPC .. A61M 2205/3337; A61M 2205/3344; A61M 2210/1007; A61M 1/06;
(Continued)

(56) References Cited

U.S. PATENT DOCUMENTS 5,349,896 A * 9/1994 Delaney, III ........ F04B 43/0054
92/103 F
6,270,474 B1 8/2001 Nuesch
(Continued)

FOREIGN PATENT DOCUMENTS

DE 202009017571 U1 5/2010
EP 0123269 A2 10/1984
(Continued)

*Primary Examiner* — Kevin C Sirmons
*Assistant Examiner* — Leah J Swanson

(57) ABSTRACT

The present application relates to a breast pump. The breast pump has a chamber (12) and a membrane (22). The membrane (22) is receivable in the chamber (12) to separate the chamber (12) into first and second spaces (23, 24). The membrane (22) is also deformable in the chamber in response to a reduction of pressure in the first space (23) to cause a reduction of pressure in the second space (24). A limiter (16) is in the chamber (12) against which the membrane (22) is locatable to limit deformation of the membrane (22).

20 Claims, 5 Drawing Sheets

(58) Field of Classification Search
CPC ...... A61M 1/062; A61M 1/064; A61M 1/072; A61M 1/066; A61M 1/069; A61M 1/0693; A61M 1/06395; A61M 1/0697; A61M 1/82
USPC .......................................................... 604/74
See application file for complete search history.

(56) References Cited

U.S. PATENT DOCUMENTS

| | | | |
|---|---|---|---|
| 7,166,087 B2 | 1/2007 | Silver | |
| 7,201,735 B2 * | 4/2007 | Atkin | A61M 1/06 604/74 |
| 2001/0047148 A1 * | 11/2001 | Suh | A61M 1/0066 604/74 |
| 2004/0001766 A1 * | 1/2004 | Maianti | A61M 1/1698 417/395 |
| 2004/0087898 A1 * | 5/2004 | Weniger | A61M 1/064 604/74 |
| 2008/0171970 A1 * | 7/2008 | Luzbetak | A61M 1/0049 604/74 |
| 2009/0254029 A1 * | 10/2009 | Tashiro | A61M 1/066 604/74 |
| 2010/0324477 A1 * | 12/2010 | Paterson | A61M 1/0072 604/74 |
| 2011/0071466 A1 | 3/2011 | Silver | |
| 2011/0221106 A1 * | 9/2011 | Reinke | F16F 13/106 267/140.13 |
| 2013/0032600 A1 * | 2/2013 | Umezaki | F16K 1/302 220/581 |
| 2014/0094748 A1 * | 4/2014 | Hong | A61M 1/06 604/74 |

FOREIGN PATENT DOCUMENTS

| | | | | |
|---|---|---|---|---|
| EP | 1502610 A1 | 2/2005 | | |
| JP | 2006015004 A | 1/2006 | | |
| JP | 2006102220 A | 4/2006 | | |
| JP | WO 2011135928 A1 * | 11/2011 | | F16K 1/302 |
| WO | WO9944650 A1 | 9/1999 | | |
| WO | WO2008057218 A2 | 5/2008 | | |
| WO | WO2011005286 A1 | 1/2011 | | |
| WO | WO2012034238 A1 | 3/2012 | | |

\* cited by examiner

BREAST PUMP

CROSS-REFERENCE TO RELATED APPLICATIONS

This patent application claims the priority benefit under 35 U.S.C. § 371 of international patent application no. PCT/IB2013/058396, filed Sep. 9, 2013, which claims the priority benefit under 35 U.S.C § 119(e) of U.S. Provisional Application No. 61/704,700 filed on Sep. 24, 2012, the contents of which are herein incorporated by reference.

FIELD OF THE INVENTION

The present invention relates to a breast pump. The present invention also relates to a breast pump system.

BACKGROUND OF THE INVENTION

Breast pumps are well known devices for extracting milk from a breast of a user. A breast pump may be used if the baby or infant is not itself able to express milk from the breast, or if the mother is separated from the baby or infant, for example, if away from the baby at work. The use of a breast pump to express milk may also be used to stimulate and increase milk production in women with a low milk supply.

Breast pumps make use of a vacuum to induce milk expression from a nursing mother's breast. The pumping action of the device draws the milk from the nipple to a collection vessel, and the pressure and/or frequency may be adjustable to the preferences of the mother.

A breast pump system generally comprises a breast pump, acting as an expression unit, and an operating unit to operate the breast pump. The expression unit has a funnel in which a user's breast is receivable, and a receptacle in which the expressed milk is collected. The operating unit comprises a vacuum pump driven by a motor. The operating unit and the expression unit may be separated from each other and connected by a tube. Alternatively, the operating unit is mounted to the expression unit.

In use, the vacuum pump applies a vacuum to the breast received in the funnel. In one arrangement, the vacuum in the funnel is created indirectly. The reduction in pressure generated by the vacuum pump acts on a membrane, also known as a diaphragm, received in a chamber in the expression unit which is deformable to cause a reduction in pressure to be generated in the funnel. Therefore, a vacuum is applied to the breast which enables milk to be expressed.

It is known to provide a breast pump system in which a cyclical pressure differential is applied to the breast. In such an arrangement, a pressure release valve is disposed in the operating unit. After a desired reduction in pressure has been established, the valve is opened to allow the vacuum acting on the membrane to be released. As the pressure from the vacuum is released, the membrane deforms back into its original position and the vacuum acting on the user's breast is reduced. By cyclically opening and closing the valve a cyclic pressure profile on the breast is achieved.

However, one problem with the above arrangement is that if the valve fails to open then the vacuum acting on the user's breast continues to increase as the vacuum pump continues to reduce the pressure acting on the membrane. Therefore, the vacuum acting on the user's breast may cause discomfort to a user and/or may exceed a safe limit. Furthermore, the prolonged and increased vacuum can cause damage to the vacuum pump, and may prevent the user from removing their breast from the vacuum pump.

It is also known that movement of the diaphragm in the chamber can cause a noise, such as a loud squeak, to be generated. This noise is typically caused by the flexible membrane coming into contact with, moving over, or moving away from contact with, the inner surface of the chamber. Such noises can prevent a mother from being able to relax and so the let-down reflex needed to ensure milk expression may be affected.

EP 0 123 269 A2 discloses a breast-milk pump with a piston that supports a dividing membrane, which is designed as a roller membrane and is tensioned between a housing surface and a transparent lid which can screwed off. A suction tube connection piece is equipped with secondary air bores and a hasp and adjustment nut for the precision setting of secondary air and suction. The dividing membrane, the lid and the suction tube connection piece can be removed, cleaned and sterilized. The piston is supported on a spring and actuated in a drive cylinder chamber by suction air and resilience.

Further exemplary breast pumps are known from WO 2012/034238 A1, WO 99/44650 A1, DE 20 2009 017571 U1 and US 2011/071466 A1.

SUMMARY OF THE INVENTION

It is an object of the invention to provide a breast pump and/or a breast pump system which substantially alleviates or overcomes the problems mentioned above.

According to the present invention, there is provided a breast pump comprising a chamber, a membrane receivable in the chamber to separate the chamber into first and second spaces, the membrane being deformable in the chamber in response to a reduction of pressure in the first space to generate a reduction of pressure in the second space, and a limiter in the chamber to limit deformation of the membrane, wherein the membrane is free to deform in the chamber between a neutral condition, in which the membrane is spaced from the limiter, and an operating condition when a predetermined reduction of pressure is imparted on the membrane in the first space of the chamber, and wherein the limiter is configured such that the membrane locates against the limiter to limit deformation of the membrane in the chamber when a reduction of pressure in the second space is equal to or exceeds a threshold value in order to restrict the pressure reduction in the second space.

An advantage of this arrangement is that by limiting the deformation of the membrane the pressure reduction in the second space is restricted, and so this allows a restriction on the vacuum that can act on a user's breast. Therefore, discomfort or injury due to prolonged or increased vacuum to a user can be prevented. Damage to the membrane due to over-extension of the membrane can also be prevented.

The limiter may be configured to limit deformation of the membrane in the chamber when a reduction of pressure in the second space is equal to or exceeds a threshold value.

The threshold value may be equal to a normal operating reduction of pressure so that the membrane locates against the limiter when the normal operating reduction of pressure is achieved.

This allows the maximum reduction in pressure generated in the second space during normal operation to be controlled by the membrane and the chamber.

The threshold value may be greater than a normal operating reduction of pressure so that the membrane is spaced from the limiter when the normal operating reduction of pressure is achieved.

This prevents the vacuum in the second space, and therefore at a user's breast, from reaching an unacceptable level. Therefore, an excessive pressure in the second chamber may be prevented when there is a failure of another feature of the breast pump, for example an air release valve or motor control. Furthermore, the membrane is prevented from impacting the limiter during normal operation.

The membrane may be biased away from the limiter when the membrane is received in the chamber. This can reduce the force required to return the membrane to its neutral position when a pressure reduction in the first space is released.

A face of the membrane exposed in the first space of the chamber may be configured to locate against the limiter when the membrane deforms to limit deformation of the membrane.

The limiter may be a wall of the chamber. Therefore, it is possible to use the arrangement of the chamber itself without the need to provide any additional components. Ease of assembly is also maximised.

The limiter may comprise one or more protuberances extending from a wall of the chamber. An advantage of this arrangement is that the limiter may be integrally formed with the chamber. Therefore, no additional components are required.

The limiter may be in the first space of the chamber.

The chamber may be formed by an upper portion and a lower portion, and the limiter may be formed by at least part of the upper portion.

The limiter and/or the membrane may define one or more channels along which air is able to flow when the membrane locates against the limiter. Therefore, it is possible to provide a better control of airflow into and out of the chamber when the membrane is urged into contact with the limiter.

The breast pump may further comprise one or more protrusions extending from a surface of the chamber, wherein the one or more channels are defined by the one or more protrusions. This means that it is possible for the or each protrusion to easily provide channels along which air is able to flow when the membrane is drawn toward the surface of the chamber.

The limiter may be one or more ribs. Therefore, the ribs are able to provide the function of limiting the deformation of the membrane whilst allowing air to flow along the or each channel.

The one or more channels may be formed in the surface of the chamber. Therefore, the channels are easily formed during manufacture.

The one or more channels may extend to a port formed in the surface of the chamber. This means that air between the membrane and a surface of the chamber is able to flow to the port when the membrane is drawn against the limiter. Furthermore, the membrane is prevented from acting as a plug when it is drawn to the port formed in the surface.

The one or more channels may extend substantially radially away from the port formed in the surface of the chamber. Therefore, air flow proximate to the surface of the chamber is easily controllable.

A surface of the chamber contactable with the membrane, and/or a surface of the membrane contactable with the chamber, may have a textured surface finish so that the noise level generated as the membrane comes into contact with, moves along, or moves away from, the chamber is minimised. This acts to reduce the noise level generated by a surface of the flexible membrane coming into contact with, or moving away from, a surface of the chamber. The textured surface finish acts to reduce the surface area of the membrane and chamber in contact with each other.

In one embodiment, the surface of the chamber contactable with the membrane may have a textured surface finish. With this arrangement the textured surface is easily formed due to the rigidity of the shell forming the chamber.

In another embodiment, the surface of the membrane contactable with the chamber may have a textured surface finish.

The chamber may comprise a sidewall against which the membrane locates prior to and/or during deformation wherein the surface having the textured surface finish is formed by the sidewall and/or the section of membrane contactable with the sidewall. Therefore, the surface area of the surface of the membrane in contact with the circumferential surface of the sidewall extending around the membrane, against which the membrane is urged, is minimised.

The surface may have a textured surface finish with an arithmetical mean roughness (Ra) of about Ra 1.6 µm.

The surface may have a textured surface finish with an arithmetical mean roughness (Ra) greater than Ra 0.8 µm.

One advantage of the above arrangement is that having a textured surface finish of greater than Ra 0.8 µm reduces the noise generated by the surface of the membrane moving over the surface of the chamber.

The surface may have a textured surface finish with an arithmetical mean roughness (Ra) of less than Ra 3.2 µm. One advantage of the above arrangement is that having a textured surface finish of less than Ra 3.2 µm restricts excessive wear of the membrane as it moves over the surface of the chamber.

In yet another embodiment, the surface of the chamber contactable with membrane and the surface of the membrane contactable with the chamber may both have a textured surface finish.

In such an embodiment, the surfaces of the chamber and the surface of the membrane may each have a textured surface finish with an arithmetical mean roughness (Ra) greater than Ra 0.4 µm. One advantage of the above arrangement is that each surface having a textured surface finish minimises the arithmetical mean roughness (Ra) required to minimise the noise generated by the surface of the membrane moving over, into contact or away from the surface of the chamber.

According to another aspect of the present invention, there is also provided a breast pump comprising a chamber, a membrane receivable in the chamber to separate the chamber into first and second spaces, the membrane being deformable in the chamber in response to a reduction of pressure in the first space to generate a reduction of pressure in the second space, and a surface in the chamber against which a membrane is locatable when the membrane has deformed wherein the surface defines one or more channels along which air is able to flow when the membrane locates against the surface.

This means that air flow between the surface and the membrane is controllable when the membrane comes into contact with the surface. Furthermore, air is prevented from being trapped against the surface, and is restricted from acting as a plug against the surface.

According to another aspect of the present invention, there is also provided a breast pump comprising a chamber, and a membrane receivable in the chamber to separate the chamber into first and second spaces, wherein the membrane is deformable in the chamber in response to a reduction of pressure in the first space to cause a reduction of pressure in the second space, and a surface of the chamber contactable with the membrane, and/or a surface of the membrane contactable with the chamber, has a textured surface finish so that the noise level generated as the membrane comes into contact with, moves along, or moves away from, the chamber is minimised.

According to another aspect of the present invention, there is also provided a breast pump breast pump system comprising a breast pump according to any of claims 1 to 14.

The breast pump system may further comprise a vacuum unit configured to generate a reduction in pressure in the first space.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
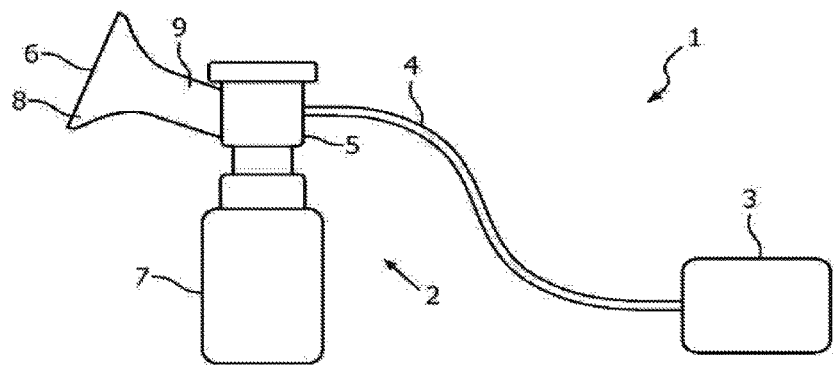
FIG. 1 is a schematic side view of a breast pump system.

A breast pump system is shown in FIG. 1. The breast pump system 1 comprises a breast pump 2, also known as an expression unit, and an operating unit 3.

The breast pump 2 and the operating unit 3 are connected by a tube 4. The tube 4 provides a fluid communication between the breast pump 2 and the operating unit 3. The tube 4 may also be used to provide an electrical connection between the breast pump 2 and the operating unit 3. For example, the tube may supply an operating signal or electrical power between the breast pump and the operating unit.

The breast pump 2 has a main body 5, a funnel 6 and a collection vessel 7. The collection vessel 7, or receptacle, collects milk expressed from a user's breast and may take the form of a feeding bottle or bag. The collection vessel 7 is attached to the main body 5 by a screw fitting, although it will be understood that alternative releasable attachment means may be used, such as clips (not shown).

The breast-receiving funnel 6 extends from the main body 5. The funnel 6 is configured to receive the breast of a user. The funnel 6 has a mouth 8 and a throat 9. The mouth 8 is open at an outer end of the funnel 6 to receive a user's breast, and the funnel 6 converges from the outer end towards the throat 9 to form a hollow recess in which a breast is received.

The main body 5 fluidly connects the funnel 6 to the collection vessel 7. A fluid passageway 10 (refer to FIG. 2) is formed through the main body 5 from the breast receiving space of the funnel 6 to the collection vessel 7. The main body 5 is formed from an outer shell. The main body 5 is integrally formed with the funnel 6, however it will be understood that the funnel 6 may be detachable. In the present arrangement the main body 5 is formed from polypropylene, although it will be understood that alternative suitable materials may be used.

The operating unit 3 comprises a controller (not shown), a power source (not shown), a motor (not shown) and a vacuum unit (not shown). The vacuum unit is configured to generate and release a pressure reduction in a vacuum path. The controller controls operation of components of the operating unit 3. The means for generating the pressure reduction and the means for releasing the pressure reduction are separate components, however it will be understood that the means for generating the pressure reduction and the means for releasing the pressure reduction may be integrally formed. In particular, in the present embodiment the vacuum unit comprises a vacuum pump (not shown) and a pressure release valve (not shown). The vacuum pump acts as a pressure reduction means. The pressure release valve acts as a means for releasing a pressure reduction.

The vacuum unit is configured to generate a pressure reduction in the vacuum path to operate the breast pump 2. That is, the vacuum pump generates a vacuum. The vacuum pump is fluidly connected to a chamber 12 (refer to FIG. 2) formed in the main body 5 of the breast pump 2 via the tube 4. The vacuum pump is generally operated by the motor (not shown).

The release valve is configured to cyclically open to release the vacuum generated by the vacuum pump. By cyclically opening and closing the valve a cyclic pressure profile is achieved. The pressure release valve (not shown) may be a solenoid valve. Operation of the pressure release valve (not shown) is controlled by the controller. Although in the present embodiment separate breast pump and operating units are provided, in other embodiments the breast pump system components such as the collection vessel, funnel, vacuum pump, electric motor and power supply, may be housed in a single body. For example, components of the operating unit may be integrated into the main body of the breast pump, removing the need for a separate operating unit.

Figure 2:
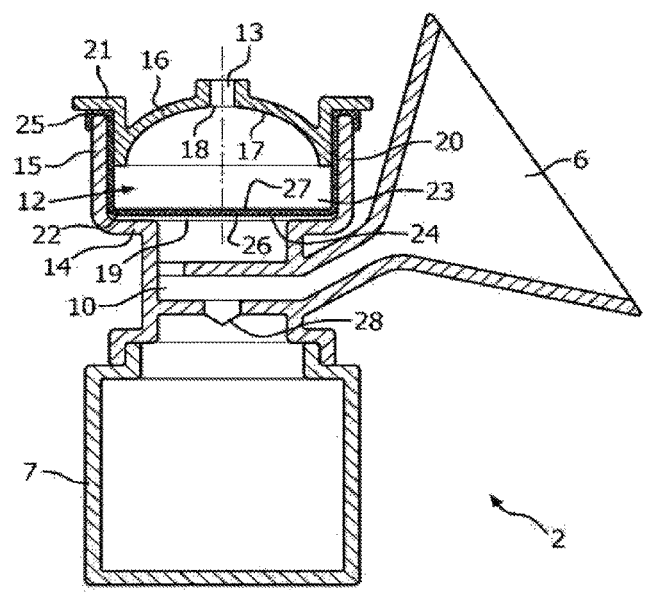
FIG. 2 is a diagrammatic cross-sectional side view of a breast pump of a breast pump system as shown in FIG. 1.
Figure 3:
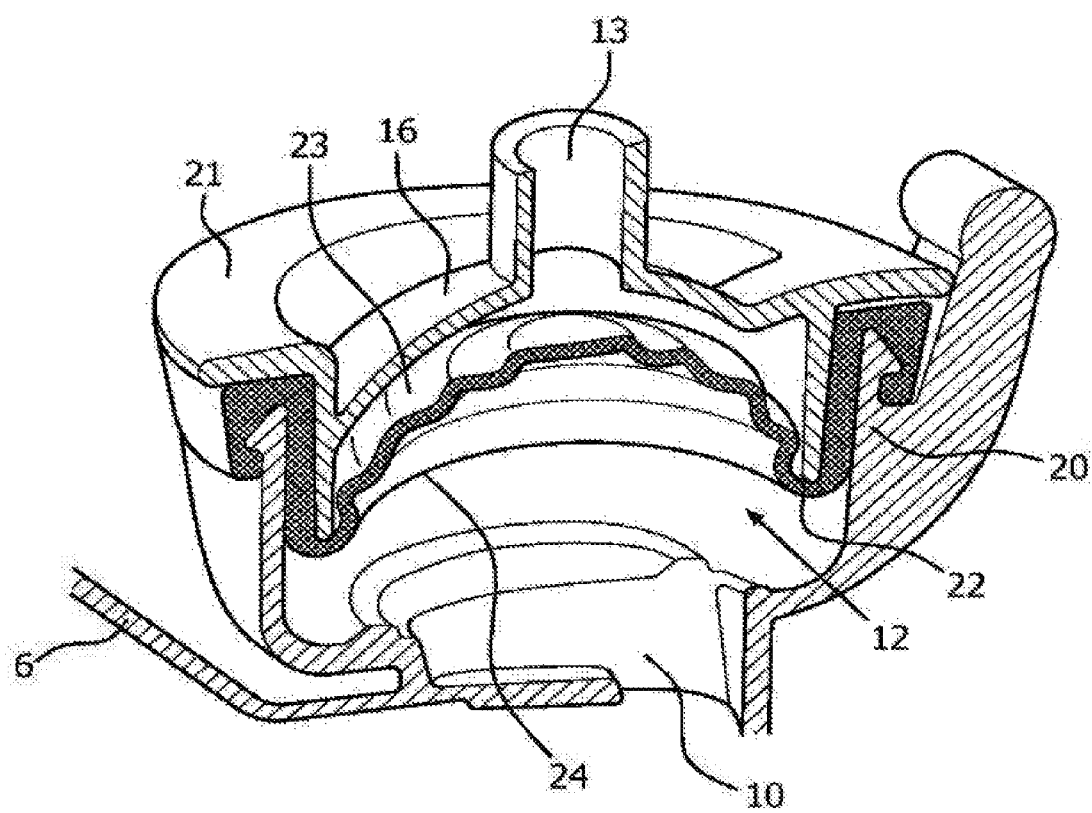
FIG. 3 is a partial cross-sectional perspective view of a breast pump as shown in FIG. 2.

Referring now to FIGS. 2 and 3, the chamber 12 is shown formed in the main body 5. The chamber 12 is formed along the fluid passageway 10. That is, the chamber 12 is in fluid communication with the fluid passageway 10 between the funnel 6 and the collection vessel 7. The chamber 12 has a vacuum port 13. The vacuum port 13 communicates with the vacuum pump (not shown) in the operating unit 3. The tube 4 is mountable to the vacuum port 13 to fluidly communicate therewith. Therefore, the vacuum pump is able to cause a pressure reduction in the chamber 12 via the port 13. The vacuum port 13 is formed at an upper end of the chamber 12.

The chamber 12 has a base 14, a sidewall 15 and an upper wall 16. The sidewall 15 extends between the base 14 and the upper wall 16. The sidewall 15 extends circumferentially around the chamber 12. The chamber is generally cylindrical in the present embodiment, however it will be understood that the shape and dimensions of the chamber 12 may vary. The base 14, sidewall 15 and upper wall 16 define an inner surface 17 of the chamber 12. An inlet 18 to the port 13 is formed through the upper wall 16. An opening 19 to the fluid passageway 10 is formed in the base 14.

In the present embodiment, the chamber 12 has lower and upper portions 20, 21 which are mountable to each other. However, it will be understood that in an alternative embodiment, the lower and upper portions 20, 21 are formed together. The lower portion 20 defines the base 14 and a lower part of the sidewall 15. The upper portion 21 defines the upper wall 16 and an upper part of the sidewall 15. The lower portion 20 is integrally formed with the funnel 6 and part of the main body 5 forming the fluid passageway 10. The upper portion 21 is a cap which is detachable from the lower portion 20. When the cap is mounted to the lower portion 20 the chamber is formed as an enclosed space. It will be understood that alternative arrangements are possible. For example, the lower portion and the funnel may be separable.

The upper wall 16 of the chamber 12 has an inner surface. In the present arrangement, the inner surface of the upper wall 16 is domed. However, it will be understood that alternative arrangements for the upper wall 16 of the chamber are envisaged. It will be understood that the profile of the inner surface may correspond to the shape of the membrane in its deformed condition. This helps ensure a consistent pressure reduction during operation of the breast pump 2.

A membrane 22 is received in the chamber 12. The membrane 22, also known as a diaphragm, is flexible. The membrane 22 separates the chamber 12 into a first space 23 and a second space 24. The first space 23 is in fluid communication with the vacuum port 13. Therefore, the vacuum pump is able to generate a pressure reduction in the first space 23. The second space 24 is in fluid communication with the fluid passageway 10 between the breast receiving space of the funnel 6 and the collection vessel 7. Therefore, a pressure reduction will be generated in the fluid passageway 10 when a pressure reduction is generated in the second space 24, as will become apparent hereinafter. A one-way valve 28 is disposed in the fluid passageway 10. The one-way valve prevents the need to draw air from the collection vessel 7 to generate a pressure reduction, and also prevents the need to provide a sealed interface between the vessel and the main body 5.

An outer rim 25 of the membrane 22 is mountable between the lower and upper portions 20, 21. When the upper portion 21 is mounted to the lower portion 20, the upper portion 21 at least partially overlaps the lower portion 20. The outer rim 25 of the membrane 22 is received between the overlap of the lower and upper portions 20, 21. Therefore, the membrane 22 is fixedly mounted in the chamber 12. This means that the membrane 22 is held in position in the chamber 12.

The membrane 22 is formed from silicone. However, it will be understood that the membrane 22 may be formed from another suitable material.

The flexible membrane 22 has a predefined shape. In the present arrangement, the membrane 22 has a substantially cup-shaped arrangement in a neutral position. That is the membrane 22 has a substantially cup-shaped arrangement when it is received in the chamber 12, but has not been deformed. However, it will be understood that the membrane 22 is not limited to a cup shaped arrangement, and may have an alternative shape.

In the present embodiment, the membrane 22 has a lower face 26 and an upper face 27. In the present embodiment, the membrane 22 is configured to invert as it deforms in response to a reduction of pressure being imparted on one side of the membrane 22 in the chamber 12. However, it will be understood that in an alternative embodiment the membrane 22 may not invert. For example, in an alternative arrangement the membrane may be formed to have a planar shape when the membrane 22 is received in the chamber 12.

When the breast pump 1 is assembled, the membrane 22 is received in the chamber 12. The outer rim 25 is disposed between the lower and upper portions 20, 21 forming the chamber 12. In the present embodiment, a lower end 30 of the upper portion 21 overlapping the lower portion 20 in the chamber 12 defines the edge of the section of the membrane 22 which is able to deform in the chamber 12.

Figure 4:
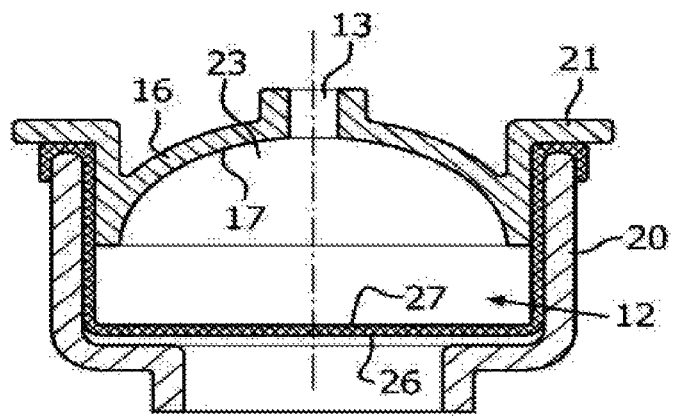
FIG. 4 is a cross-sectional side view of a chamber and membrane of a breast pump as shown in FIG. 2 in a neutral condition.

The membrane is initially in its neutral, or undeformed, condition in the chamber 12. In this position, the lower face 26 of the membrane 22 is disposed proximate to, but slightly spaced from, the surface of the chamber 12, for example the lower part of the sidewall 15. The lower face 26 of the membrane 22 may locate against the surface of the chamber 12 in the membrane's neutral condition. The membrane 22 is shown in an undeformed condition in FIG. 4.

The vacuum port 13 is fluidly connected to the tube 4, such that the first space 23 is in fluid communication with the operating unit 3, and therefore the vacuum pump (not shown). A user inserts their breast into the mouth 8 of the funnel 6 such that a fluid seal is formed between the funnel 6 and the breast, with the user's nipple received in the neck 9 of the funnel 6.

The user then operates the breast pump system. The controller operates the vacuum unit (not shown) in response to a user input to operate the breast pump.

The vacuum unit generates a pressure reduction in the first space 23 of the chamber 12 by fluid communication through the tube 4. When a vacuum condition is produced in the first space 23 of the chamber 12, the membrane 22 is induced to deform in the chamber 12 due to the pressure differential between the first space 23 and the second space 24 in the chamber 12. Therefore, the membrane 22 deforms in the direction of the first space 23. That is, the membrane 22 distends towards the upper wall of the chamber 12.

Figure 5:
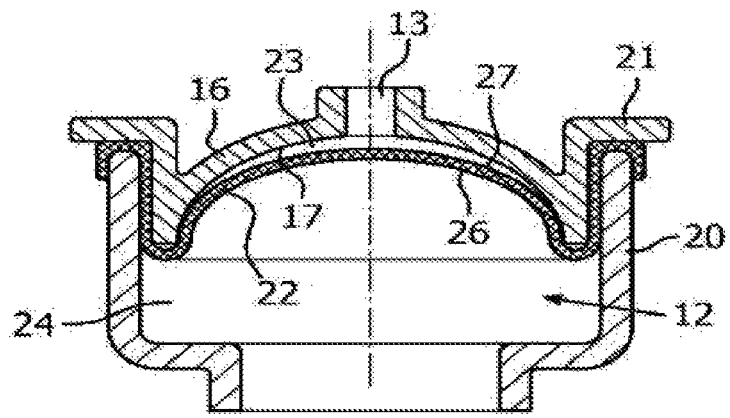
FIG. 5 is a cross-sectional side view of a chamber and membrane shown in FIG. 4 in a deformed condition.

As the membrane 22 deforms, it is drawn in the direction of the first space 23. Therefore, the distension of the membrane 22 causes a pressure reduction in the second space 24 of the chamber 12. As a breast is received in the mouth 8 of the funnel 6, and forms a fluid seal therewith, a closed system is formed between the neck 9 of the funnel 6, the fluid passageway 10 and the second space 24 of the chamber 12. Therefore, when the membrane 22 deforms in the chamber 12 so that a pressure reduction is caused in the second space 24, a vacuum is generated in the fluid passageway 10 and the funnel 6. This vacuum acts on the user's breast to induce the expression of milk from a user's nipple which is received in the funnel 6. An operating vacuum condition of the membrane 22 is shown in FIG. 5, in which the membrane 22 has deformed to generate a vacuum in the second space 24 and therefore at a user's breast During normal operation, the controller operates the pressure release valve of the vacuum unit (not shown) to release the reduction in pressure in the first space 23 when a predetermined pressure is achieved. When the vacuum is released in the first space 23, the membrane 22 is urged to return to its neutral condition. That is, the membrane 22 is urged to return to its neutral condition by moving in the direction of the second space 24 of the chamber 12 by the pressure difference created on either side of the membrane 22. The membrane 22 may also be urged to distend back towards its neutral condition due to the resilience of the membrane. This causes the vacuum in the second space 24 of the chamber 12, and therefore at the user's breast, to be released. The controller then closes the pressure release valve and a reduction in pressure is again generated in the first space 23 by the vacuum pump and the membrane 22 is induced to distend in the direction of the first space 23. In one embodiment, the membrane inverts as the membrane deforms. However in an alternative embodiment the membrane does not invert.

The vacuum is applied to the breast at intervals. That is, the reduction is pressure is generated on a cyclic basis. After a vacuum has been established, the pressure from the vacuum is released by the use of the pressure release valve, which is temporarily opened. As the pressure from the vacuum is released, the membrane deforms back into its original condition. Thus, the breast pump 1 uses a cyclic pressure profile in order to express milk from the breast.

In normal operation the vacuum should be released after each pumping cycle, by opening the release valve. The pressure release valve may be a mechanical or an electromechanical valve, for example a solenoid valve. However, if for any other reason the vacuum has not been released, or is only partially released, for instance because the release valve has failed to open or an inlet to the valve has become blocked, the vacuum unit continues to reduce the pressure in the first space 23. This will cause the membrane 22 to be induced to continue to deform beyond its normal vacuum condition.

Specifically, if the vacuum is not released, the reduction in pressure in the first space 23 will exceed the predetermined reduction in pressure. Therefore, the membrane 22 will be induced to distend in the chamber 12 beyond its normal operating condition. This additional deforming of the membrane 22 will cause a greater reduction in pressure in the second space 24 of the chamber 12, and so the vacuum at the user's breast may reach unacceptable levels. That is, the vacuum generated at a user's breast may cause discomfort or injury to the user.

Figure 6:
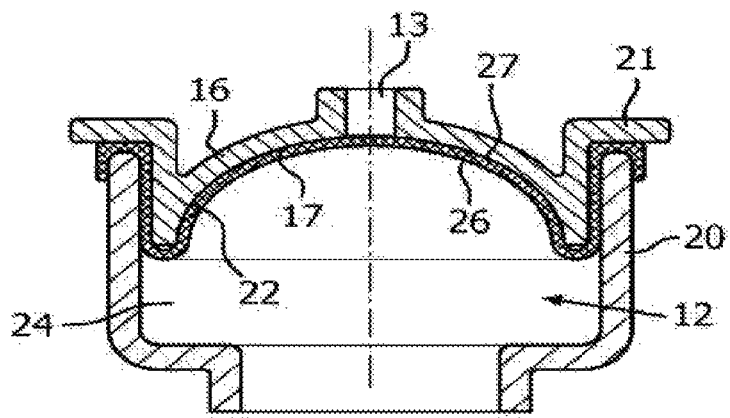
FIG. 6 is a cross-sectional side view of a chamber and membrane shown in FIG. 4 in another deformed condition.

In the present embodiment, the upper wall 16 acts as a limiter against which the membrane 22 is locatable to limit deformation of the membrane 22 in the chamber 12 when a reduction in pressure is imparted on the membrane 22 so that the pressure in the second space, and therefore at the breast, is equal to or exceeds a normal operating threshold value. That is, the membrane 22 is free to deform in the chamber 12 between a neutral condition (refer to FIG. 4) and an operating condition (refer to FIG. 5) when a predetermined reduction in pressure is imparted on the membrane 22 in the first space 23 of the chamber 12. The upper wall 16 forms a surface of the chamber. Furthermore, the upper wall 16 is exposed in the first space 23 of the chamber 12 when the membrane 22 is received in the chamber 12. The chamber 12 is configured so that the upper wall 16 is spaced from the upper face 27 of the membrane when the membrane 22 is in its deformed condition and the pressure in the second space is at the normal operating pressure. However, the upper wall 16 is configured to be disposed proximate to the upper face 27 of the membrane when the membrane 22 is in its deformed condition in response to a pressure being imparted on it so that, if the reduction in pressure in the second space exceeds a threshold value, the upper face 27 of the membrane 22 abuts against the upper wall 16 (refer to FIG. 6).

When the membrane 22 locates against the upper wall 16, the upper wall 16 prevents further deformation of the membrane 22. This means that further pressure reduction in the second space 24 is prevented, because it is not possible for the membrane 22 to further distend in a direction away from the second space 24. Therefore, the vacuum imparted on a user's breast is prevented from exceeding the threshold value.

It will be understood that in some instances the reduction in pressure that can achieved in the second space may vary slightly dependent on the size of the breast received in the mouth 8 of the funnel 6. In such an arrangement, it will be understood that the, the threshold value is not a single value but is a pressure reduction range that is equal to or exceeds a normal operating threshold value. The pressure reduction range may be determined to be a safe distance from the safety limit.

By providing a limiter against which the membrane locates when the threshold pressure reduction in the second space is met or exceeded, it is possible for embodiments to avoid an excessively high vacuum developing at the breast pump funnel even when a normal release mechanism has failed. Such embodiments can allow a powerful pump to be used, capable of reaching a desired vacuum level more quickly, without a risk of a high vacuum being developed at the breast pump funnel if the vacuum is not correctly released at the end of each cycle.

In the above described embodiment the upper wall of the chamber is configured to be spaced from the upper face of the membrane during normal operation of the breast pump, so that the upper wall does not restrict deformation of the membrane. An advantage of this arrangement is that a consistent airflow is achieved in the first space of the chamber, and the membrane is prevented from forming a plug against the port in the upper wall.

However, in an alternative arrangement the upper wall may be configured to limit deformation of the membrane during a normal operating condition. That is, the chamber may be configured to ensure that the membrane locates against the upper wall during a normal operating cycle of the breast pump. In such an arrangement, the upper wall is configured to limit deformation of the membrane when a normal operating reduction of pressure is reached in the second space of the chamber. Therefore, the upper wall acts to control the maximum vacuum achievable during operation of the breast pump. This means that the maximum reduction in pressure at the breast cannot exceed its normal operating threshold.

Although in the above embodiment the upper wall is used as a limiter against which the membrane locates in the chamber when the threshold pressure reduction is exceeded, and so limit the vacuum generated at a user's breast, even when a normal vacuum release mechanism has failed, it will be understood that alternative arrangements are possible. In an alternative arrangement, protuberances, such as ribs extend from the upper wall against which the membrane is locatable to limit deformation of the membrane. Alternatively, an insert is received in the chamber against which the membrane is locatable to limit deformation of the membrane. The insert may be mountable to the upper portion, or mountable between the upper portion and the lower portion when they are brought together.

It is also possible for the limiter to be formed by an element extending across the chamber against which the membrane is locatable when it deforms to limit deformation of the membrane.

A further aspect of the breast pump system will now be described with reference to FIG. 7. The features of this aspect of the breast pump system can be implemented in any of the breast pump systems described above with reference to FIGS. 1, 2, 4 and 6, or in any conventional breast pump system not including the features of the above-described systems. The general arrangement is described above and so a detailed description will be omitted herein.

Figure 7:
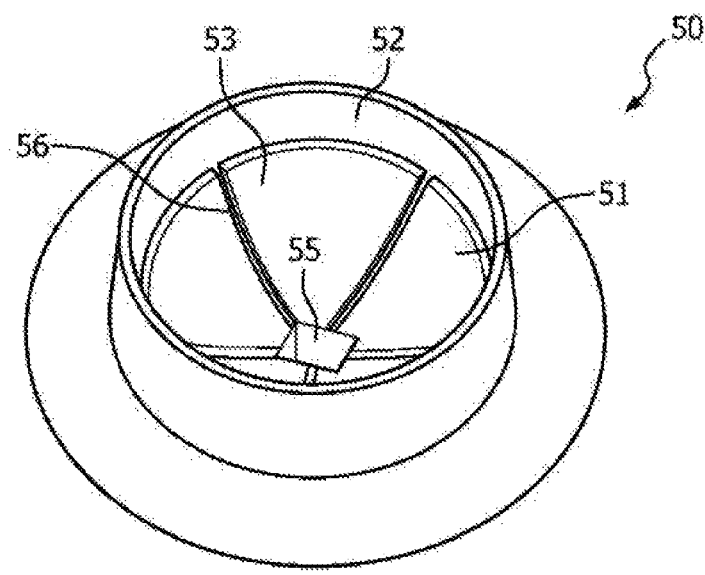
FIG. 7 is a perspective view of a top portion or cap of a chamber of a breast pump as shown in FIG. 2.

An upper portion 50 of a breast pump is shown in FIG. 7. The upper portion 50 of the chamber of the breast pump shown in FIG. 7 is similar to the upper portion of the chamber illustrated in FIGS. 2 to 6, and is provided for use with in a breast pump system such as that shown in FIG. 1. The upper portion 50 of the breast pump is mountable to a lower portion (refer to FIG. 2). However, it will be understood that in an alternative embodiment the upper portion 50 may be integrally formed with a corresponding lower portion to form the chamber. The upper portion 50 defines an upper wall 51 of the chamber. The upper portion 50 also defines an upper part of a sidewall 52 of the chamber. The upper portion 50 is a cap which is mountable to the lower portion of the chamber. When the cap is mounted to the lower portion the chamber is formed as an enclosed space.

The upper wall 51 of the chamber has an inner surface 53. In the present arrangement, the inner surface 53 of the upper wall 51 is domed. However, it will be understood that alternative arrangements for the upper wall 51 of the chamber are envisaged.

The upper portion 50 is formed from polypropylene. However, it will be understood that the membrane 22 may be formed from another suitable material, for example another rigid material.

The upper portion 50 of the chamber 12 has a vacuum port 55. The vacuum port 55 communicates with the vacuum pump (not shown) in an operating unit of the breast pump system. A tube (refer to FIG. 1) is mountable to the vacuum port 55 to fluidly communicate therewith. Therefore, the vacuum pump is able to cause a pressure reduction in the chamber via the port 55. The vacuum port 55 is formed through the upper portion 50. The vacuum port 55 is formed through the surface 53 of the upper wall 51.

Elongate recesses 56 are formed in the inner surface 53. The elongate recesses 56 act as channels. The channels allow the passage of air along them. Five elongate recesses are shown, however it will be understood that the number of elongate recesses may vary.

Each elongate recess 56 has a base and side walls extending between the base and the inner surface 53. The elongate recesses may be arcuate in cross-section. Each elongate recess 56 communicates with the port 55.

When the breast pump is assembled, the upper portion 50 is mounted to the lower portion and a membrane is received in the chamber. The membrane, and arrangement of the membrane in the chamber, has been described in detail above and so a detailed description will be omitted herein. When the membrane is induced to deform in the chamber due to the pressure differential between the first space and the second space in the chamber, the membrane distends towards the upper wall 51. Therefore, the distension of the membrane causes a pressure reduction in the second space of the chamber and a vacuum is generated to act on the user's breast disposed in the funnel. Therefore, the vacuum acts to induce the expression of milk from a user's nipple.

After a vacuum has been established, the pressure from the vacuum is released by a pressure release valve which is temporarily opened. As the pressure from the vacuum is released, the membrane deforms back into its original condition. Thus, the breast pump uses a cyclic pressure profile to express milk from the breast.

However, when the membrane deforms towards the upper wall 51 of the chamber, it may come into contact with the upper wall 51. As described above, this may limit deformation of the membrane, and therefore limit the air volume which can be sucked out of the chamber.

The channels formed by the elongate recesses 56 allow air disposed between the membrane and the surface of the upper wall 51 to flow to the port 55. The channels allow all the air in the chamber to be evacuated from the chamber prior to the membrane acting as a plug over the port 55. That is, the membrane is prevented from being drawn to the port and blocking the port whilst a section of the membrane is spaced from the surface of the upper wall 51. If the membrane acts as a plug in an early stage of the pressure reduction in the first space of the chamber, a lower volume of air is drawn from the first space of the chamber, and so the deformation of the membrane is limited which leads to a lower volume being generated at a user's breast.

The channels, or flow leaders, create an air channel from the whole volume area between the surface 53 of the upper wall 51 and the membrane to the port 55. Therefore, air traps are prevented.

An advantage of the above arrangement is that the channels ensure that a consistent volume of air is drawn from the first space of the chamber on each vacuum cycle, which leads to a consistent pressure reduction being formed at a user's breast.

Similarly, upon releasing the vacuum, the channels prevent the membrane from being stuck against the inner surface of the upper wall 51 due to a vacuum being formed between the membrane and the upper wall 51. Therefore, the membrane is allowed to return completely to the relaxed state. So in the following cycle the membrane starts from its neutral condition.

Figure 9:
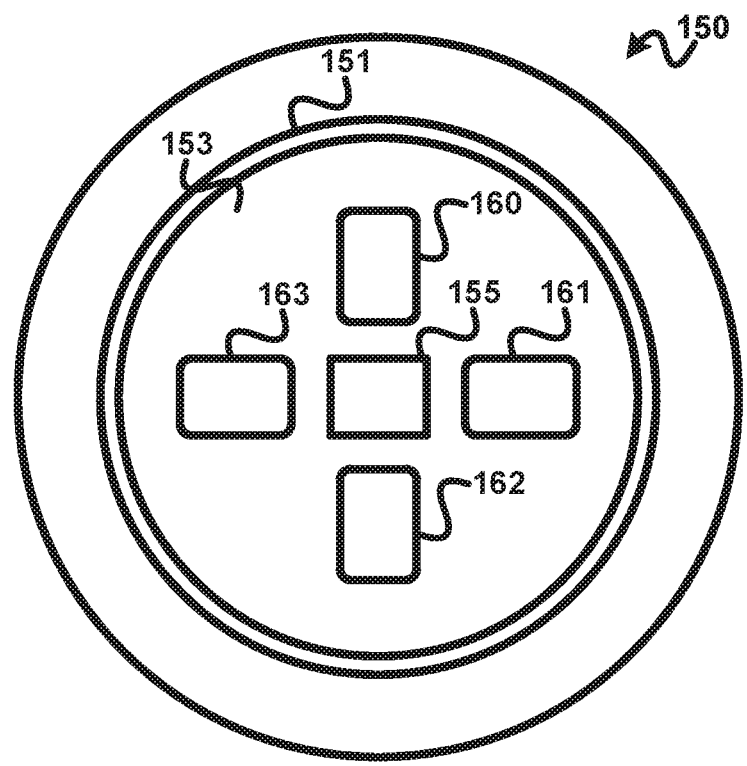
FIG. 9 is a bottom view of an alternative top portion or cap of a chamber of a breast pump as shown in FIG. 2.
Figure 10:
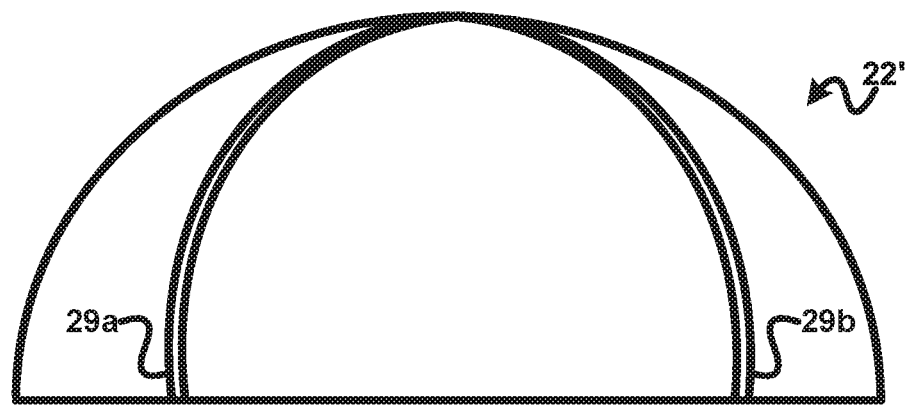
FIG. 10 is a side view of a channels in a membrane.

Although in the above described embodiment, the channels are formed by recesses formed in the surface of the chamber, it will be understood that the channels may be formed by alternative arrangements. In one alternative arrangement, as shown in FIG. 9, ribs 160-163 are formed on an inner surface 153 of an upper wall 151. The ribs 160-163 upstand from the upper wall 151 and encircle a vacuum port 155. When the membrane locates against the ribs 160-163, a channel is formed alongside each rib 160-163 which provides for the passage of air between the inner surface 153 of the upper wall 151 and the surface of the membrane. It will also be understood that an alternative protrusion or protrusions may be used. Further, as shown in FIG. 10, channels 29 in a membrane 22' shown in a dome position.

Although in the above described embodiment, the channels are shown to have parallel side walls, it will be understood that the arrangement of the channels are not limited thereto. For example, one or more channels may be formed to have a petal shaped arrangement in which the side walls of the channels distend away from each other in a central section of the channel. Alternatively, one or more channels may have sidewalls that diverge or converge toward each other from an outer edge.

Although in the above arrangement the channels are shown to extend in a substantially radial direction from the port, it will be understood that the or each channel may have an alternative arrangement. For example, the or each channel may have a helical arrangement around the wall of the chamber.

A further aspect of the breast pump system will now be described with reference to FIG. 8. The features of this aspect of the breast pump system can be implemented in any of the breast pump systems described above with reference to FIGS. 1, 2, 4 and 6, or in any conventional breast pump system not including the features of the above-described systems.

Figure 8:
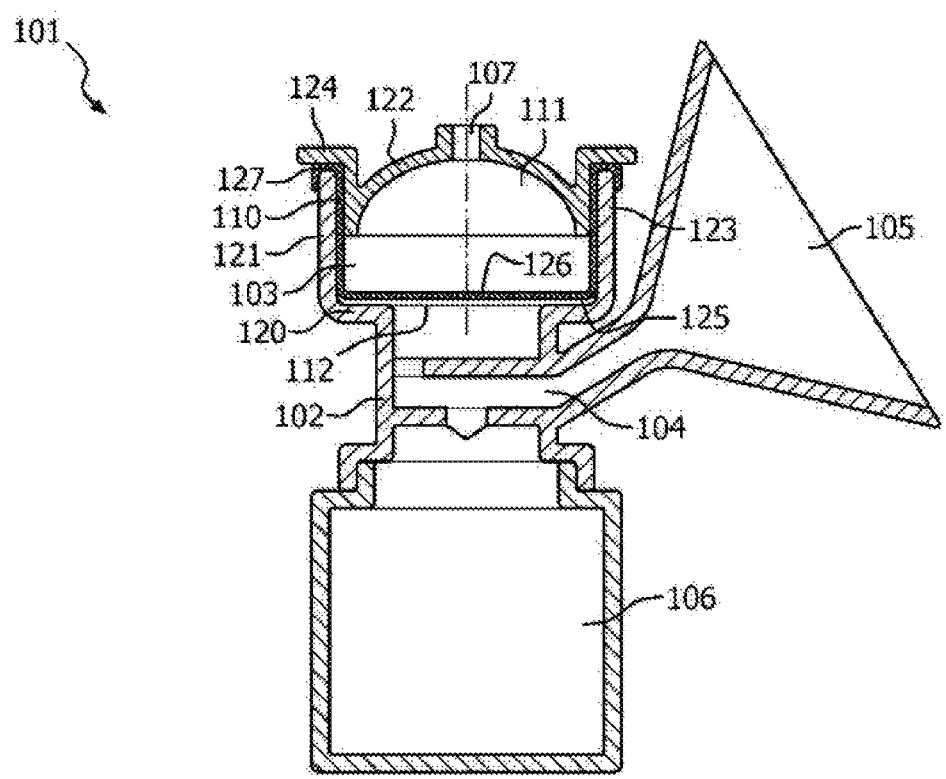
FIG. 8 is a diagrammatic cross-sectional side view of another embodiment of a breast pump of a breast pump system as shown in FIG. 1.

A breast pump 101 is illustrated in FIG. 8. The breast pump 101 is similar to the breast pump illustrated in FIG. 1, and is provided for use with in a breast pump system such as that shown in FIG. 1. The breast pump 101 has a main body 102 in which a chamber 103 is defined. The chamber 103 is formed along a fluid passageway 104 between a funnel 105 for receiving a user's breast and a collection vessel 106. The chamber 103 has a vacuum port 107. The vacuum port 107 communicates with the vacuum pump in an operating unit, similar to the operating unit described in the above embodiments. Therefore, the vacuum pump is able to cause a pressure reduction in the chamber 103. The vacuum port 107 is formed at the upper end of the chamber 103.

A membrane 110 is received in the chamber 103. The membrane 110, also known as a diaphragm, is flexible. The membrane 110 separates the chamber 103 into a first space 111 and a second space 112. The first space 111 is in fluid communication with the vacuum port 107. Therefore, a pressure reduction is generated in the first space 111 by the vacuum pump. The second space 112 is in fluid communication with the fluid passageway 104 between the breast receiving space of the funnel 105 and the collection vessel 106.

When a pressure reduction or vacuum is generated in the first space 111, the membrane 110 deforms and is drawn in the direction of the first space 111. Therefore, a pressure reduction is produced in the second space 112 of the chamber 103 due to the deformation of the membrane 110. When a breast is received in the mouth of the funnel, a pressure reduction is formed in the funnel 105 which acts on the user's breast and urges milk to be expressed therefrom.

The chamber 103 has a base 120, a sidewall 121 and an upper wall 122. The sidewall 121 extends between the base 120 and the upper wall 122. The sidewall 121 extends circumferentially around the chamber 103. The chamber 103 is formed from lower and upper portions 123, 124 which are mountable to each other. The lower portion 123 defines the base 120 and a lower part of the sidewall 121. The upper portion 124 defines the upper wall 122 and an upper part of the sidewall 121. An outer rim of the membrane 110 is mountable between the upper and lower portions 123, 124. Therefore, the membrane 110 is fixedly mounted in the chamber 103. This means that the membrane 110 is held in position in the chamber 103.

The vacuum port 107 communicates with the chamber 103 through the upper wall 122 and the fluid passageway 104 communicates with the chamber 103 through the base 120. The base 120, sidewall 121 and upper wall 122 define an inner surface of the chamber 103.

In the present embodiment, the main body 102 forming the chamber is formed from polypropylene. The flexible membrane 110 is formed from silicone. However, it will be understood that the chamber 103 and membrane 110 may be formed form other suitable materials.

The flexible membrane 110 has a predefined shape. In the present arrangement, the membrane 110 has a substantially cup-shaped arrangement in its neutral position, i.e. when it has not been deformed by a reduced pressure in the first space 111. The membrane 110 has a lower face 125 and an upper face 126. A lip 127 extends from the free end of a membrane side wall. However, it will be understood that the membrane may be formed to have an alternative shape. With the present arrangement, the lip 127 is mounted between the lower and upper portions 123, 124 forming the chamber 103. In the present embodiment, the membrane inverts as the membrane 110 deforms. However, it will be understood that in an alternative embodiment the membrane 110 does not invert.

The sidewall 121 has a textured surface. That is, at least a section of the surface of the chamber has a textured surface. In the present embodiment, the lower part of the sidewall 121 is configured to have a textured surface. The textured surface may extend over all of the surface of the lower part of the sidewall 121, or only a section of it. The section may comprise the section of the sidewall which will come into contact with the membrane 110. The textured surface may cover all or part of the chamber surface. For example, there can be a series of repeated patterns extending around the circumference of the chamber each of which has a surface texture.

The textured surface is formed from a textured surface finish having an arithmetical mean roughness (Ra) in the range of Ra 0.8 µm to Ra 3.2 µm. It has been found that a completely smooth, i.e. high gloss finish (±Ra 0.05 µm) can result in a high squeaking noise being caused by the flexible membrane 110 and the surface of the chamber sticking to each other when the membrane 110 is deformed in the chamber 103.

It has also been found that a surface with a high roughness, for example greater than Ra 3.2 µm, may result in higher wear of the membrane 110 as it moves over the surface. Therefore, a surface finish in the range of Ra 0.8 µm to Ra 3.2 µm will minimise the noise created by the deflection of the membrane 110 relative to the surface whilst minimising wear of the membrane due to the surface.

In one embodiment, the surface having a textured surface has an arithmetical mean roughness (Ra) of Ra 1.6 µm. It has been determined that a surface with this value of arithmetical mean roughness produces minimal noise during use of the breast pump whilst minimising wear of the membrane.

The textured surface is formed by in-mould texturing. That is, the textured surface is formed by adding a texture to the tool to form the main body 102, for example a spark erosion texture. Alternatively, the textured surface is formed following production of the main body, for example by sandblasting. Alternative methods of forming the textured surface may be used.

When the breast pump is assembled, the membrane 110 is received in the chamber 103. The lower face 125 of the membrane 110 is disposed proximate to, but slightly spaced from, the surface of the chamber 103, for example the lower part of the sidewall 121. The membrane 110 is then in its neutral, or undeformed, position. Alternatively, the lower face 125 of the membrane 110 may be located against the surface of the chamber 103 in its neutral position.

When the breast pump 101 is operated, a pressure reduction is caused in the first space 111 and so the membrane 110 is urged to deform. As the membrane 110 starts to deform the membrane 110 is either urged into contact with the surface of the chamber 103, or is initially in contact with the surface of the chamber 103. It will be understood that the section of the surface of the chamber 103 that comes into contact with the membrane 110 is configured to have a textured surface.

As the membrane 110 is urged to further deform, the lower face 125 of the membrane 110 is drawn away from and/or over the surface of the sidewall 121 as the membrane 110 is urged to deform due to a reduction in pressure in the first space 111 of the chamber 103. Similarly, it will be understood that the lower face 125 of the membrane 110 is moved against and/or over the face of the sidewall 121 as the membrane 110 is urged to return to its neutral position due to a release of the reduction in pressure in the first space 111 of the chamber 103.

As the membrane 110 comes into contact with, moves along, or moves away from, the textured surface the area of contact formed between the membrane 110 and the surface of the chamber 103 is minimised. Therefore, the noise generated due to the membrane 110 and the surface of the chamber 103 moving relative to each other is minimised. For example, a quack or squeaking noise is reduced. This noise is formed by a stick-slip phenomenon caused by the membrane sticking and slipping on the inner surface of the surface of the chamber as the membrane deforms and/or by the membrane sticking and slipping against itself as it deforms. The effect may be caused by rubbing on a microscopic scale. When a textured surface finish is formed on the surface of the membrane and/or the chamber there is less sticking between the membrane 110 and the surface of the chamber 103 due to the reduced surface area.

One advantage of a section of the chamber having a textured surface is that the reduction in surface area contact between the membrane and the surface of the chamber will minimise the friction caused between the membrane and the chamber. Therefore, it will be easier to move the membrane in the chamber. This means that less energy is required to deform the membrane in the chamber and also to return the membrane to its neutral position.

Although in the above embodiment the textured surface is formed on the lower part of the sidewall between the base and the membrane, it will be understood that the textured surface may also, or alternatively, be formed on the upper part of the sidewall between the membrane and the upper wall. This arrangement minimises any noise created through contact between the membrane and the upper part of the sidewall.

Although in the above embodiments the textured surface is formed on the sidewall of the chamber, it will be understood that the textured surface may be formed on any surface of the main body against over which the membrane comes into contact, or moves away from, during deformation of the membrane. In particular, the base and/or the upper wall may also have a textured surface.

Although the textured surface finish is formed on a surface on the chamber in the above described embodiments, it will also be understood that the textured surface may also, or alternatively, formed on the surface of the membrane. This would have the same effect of reducing the contact area between the surface of the membrane and the surface of the chamber. The textured surface may be formed on all or part of the lower face of the membrane, and/or all or part of the upper face of the membrane.

Although in the above described embodiments the vacuum unit is provided with separate means for generating the pressure reduction in the vacuum path and releasing the pressure reduction in the vacuum path, it will be understood that they may be integrated. In another embodiment, the vacuum unit comprises a piston slidably received in a piston chamber or cylinder. The piston acts as a reciprocating element. The piston forms a fluid seal in the chamber. The piston chamber forms part of the vacuum path. The piston is reciprocally operated, for example, by a crankshaft and a motor. When the piston is drawn along the piston chamber, the movement of the piston acts to generate a pressure reduction in the vacuum path. Therefore, a vacuum may be produced at the user's breast. When the piston moves in the opposite on its return stroke the pressure reduction in the chamber is released. However, in the event that the piston becomes stuck or the motor fails, for example, then the piston will not release the pressure reduction in the vacuum path. That is, the vacuum unit will fail to release the pressure reduction in the vacuum path. If this occurs, then the leakage aperture provided in the vacuum path will allow a controlled release of the pressure reduction in the vacuum path.

In the above embodiment, it will be understood that the vacuum path is formed between the piston and a user's breast when the breast pump system is assembled and a user's breast is received in the funnel. The vacuum unit may be disposed in the operating unit or may be housed in the breast pump.

In another embodiment, the vacuum unit is formed by the membrane and a means of mechanically deforming the membrane. The membrane acts as a reciprocating element. For example, a rod may be attached to the deformable membrane which is movable in a reciprocal manner by a motor. With such an arrangement the deformation of the membrane from its neutral condition generates a pressure reduction in the vacuum path. Subsequently, the return of the membrane to its neutral condition releases the pressure reduction in the vacuum path. In this embodiment it will be understood that the vacuum path is formed between the membrane and a user's breast when the breast pump system is assembled and a user's breast is received in the funnel. However, in the event that the membrane does not return to its neutral condition, for example due to failure of the motor, then the membrane will not release the pressure reduction in the vacuum path. That is, the vacuum unit will fail to release the pressure reduction in the vacuum path. If this occurs, then the leakage aperture provided in the vacuum path will allow a controlled release of the pressure reduction in the vacuum path. The membrane may be the membrane described in the above embodiments or may be another membrane disposed separately.

In the above two embodiments, it will be understood that no pressure release valve is required because the reduction in pressure is released by the valve or membrane returning to its neutral position.

It will be appreciated that the term "comprising" does not exclude other elements or steps and that the indefinite article "a" or "an" does not exclude a plurality. A single processor may fulfil the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:
1. A breast pump, comprising:
a chamber defined by an upper portion and a lower portion, wherein the upper portion includes an upper wall of the chamber and an upper part of a sidewall of the chamber, wherein the lower portion includes a lower part of the sidewall and a base of the chamber, wherein a lower end of the upper part of the sidewall extends into the lower part of the sidewall and an upper end of the upper part of the sidewall at least partially overlaps an upper end of the lower part of the sidewall, and wherein the chamber has a vacuum port formed in the upper wall of the chamber;

a membrane including a first section mounted between the upper part of the sidewall and the upper end of the lower part of the sidewall with the first section of the membrane wrapping around the upper end of the lower part of the sidewall and further including a second section receivable in the chamber to separate the chamber into first and second spaces, wherein the second section of the membrane is deformable in the chamber in response to a reduction of pressure in the first space; and a limiter in the first space of the chamber to limit deformation of the second section of the membrane, wherein the second section of the membrane is free to deform in the chamber between:

a neutral condition, in which the second section of the membrane is at a set position such that the second section of the membrane is proximate to a surface of the base of the chamber, an operating condition in which the second section of the membrane is deformed to a set position that is proximate to a surface of the upper wall of the chamber and spaced from the limiter, wherein the operating condition corresponds to when a predetermined reduction of pressure is imparted on the second section of the membrane in the first space of the chamber, and wherein the second section of the membrane is configured to cyclically move between the neutral condition and the operating condition during a pumping cycle, and a limited condition in that the limiter is configured such that the second section of the membrane locates against the limiter to limit deformation of the second section of the membrane in the chamber when a reduction of pressure in the second space is equal to or exceeds a threshold value in order to restrict the pressure reduction in the second space, characterized in that one of:

the limiter includes at least one protrusion extending from the upper wall of the chamber relative to the vacuum port within the first space of the chamber to define at least one air channel between the upper wall of the chamber and the second section of the membrane when the second section of the membrane locates against the limiter, or the limiter includes at least one recess formed within the upper wall of the chamber relative to the vacuum port within the first space of the chamber to define at least one air channel between the upper wall of the chamber and the second section of the membrane when the second section of the membrane locates against the limiter.

2. The breast pump according to claim 1, wherein the threshold value of the reduction of pressure is greater than a normal operating reduction of pressure so that second section of the membrane is spaced from the limiter when the normal operating reduction of pressure is achieved.

3. The breast pump according to claim 1,
wherein the second section of the membrane locates against the lower part of the sidewall prior to deformation and locates against the upper part of the sidewall during deformation; and
wherein the upper part of the sidewall has a textured surface finish, the lower part of the sidewall has a textured surface finish, and/or the second section of membrane contactable with the sidewall has a textured surface.

4. The breast pump according to claim 1, wherein a surface of the second section of the membrane contactable with the chamber has a textured surface finish with an arithmetical mean roughness (Ra) between Ra 0.4 µm and Ra 3.2 µm for minimizing a noise level generated as the second section of the membrane comes into contact with, moves along, or moves away from, one or more of the walls of the chamber.

5. The breast pump according to claim 1, wherein a surface of the chamber contactable with the second section of the membrane has a textured surface finish with an arithmetical mean roughness (Ra) between Ra 0.4 µm and Ra 3.2 µm for minimizing a noise level generated as the second section of the membrane comes into contact with, moves along, or moves away from, the one or more walls of the chamber.

6. The breast pump according to claim 1, wherein the vacuum port is located in a center of the upper wall of the chamber.

7. The breast pump according to claim 6, wherein one recess or each recess of the at least one recess extends from the vacuum port along the upper wall of the chamber.

8. The breast pump according to claim 1, wherein one recess or each recess of the at least one recess extends from the vacuum port along the upper wall of the chamber to the upper part of the sidewall of the chamber.

9. The breast pump according to claim 8, wherein a plurality of recesses partitions the upper wall of the chamber to define a plurality of air channels between the upper wall and the second section of the membrane when the second section of membrane locates against the limiter.

10. The breast pump according to claim 1, wherein the at least one protrusion is a plurality of ribs upstanding from an inner surface of the upper wall of the chamber to define a plurality of air channels between the upper wall and the second section of the membrane when the second section of the membrane locates against the limiter.

11. The breast pump according to claim 1, wherein the membrane wraps around the upper end of the lower part of the sidewall such that an outer edge of the membrane is located exterior to the chamber.

12. A breast pump system, comprising:
the breast pump according to claim 1; and
an operating unit connectable to the breast pump for deforming the second section of the membrane between the neutral position and the operating condition.

13. The breast pump system according to claim 12, wherein the threshold value of the reduction of pressure is greater than a normal operating reduction of pressure so that second section of the membrane is spaced from the limiter when the normal operating reduction of pressure is achieved.

14. The breast pump system according to claim 12,
wherein the second section of the membrane locates against the lower part of the sidewall prior to deformation and locates against the upper part of the sidewall during deformation; and wherein the upper part of the sidewall has a textured surface finish, the lower part of the sidewall has a textured surface finish, and/or the second section of membrane contactable with the sidewall has a textured surface.

15. The breast pump system according to claim 12, wherein a surface of the second section of the membrane contactable with the chamber has a textured surface finish with an arithmetical mean roughness (Ra) between Ra 0.4 μm and Ra 3.2 μm for minimizing a noise level generated as the second section of the membrane comes into contact with, moves along, or moves away from, one or more of the walls of the chamber.

16. The breast pump system according to claim 12, wherein a surface of the chamber contactable with the second section of the membrane has a textured surface finish with an arithmetical mean roughness (Ra) between Ra 0.4 μm and Ra 3.2 μm for minimizing a noise level generated as the second section of the membrane comes into contact with, moves along, or moves away from, the one or more walls of the chamber.

17. The breast pump system according to claim 12, wherein one recess or each recess of the at least one recess extends from the vacuum port along the upper wall of the chamber to the upper part of the sidewall of the chamber.

18. The breast pump system according to claim 17, wherein a plurality of recesses partitions the upper wall of the chamber to define a plurality of air channels between the upper wall and the second section of the membrane when the second section of membrane locates against the limiter.

19. The breast pump system according to claim 12, wherein the at least one protrusion is a plurality of ribs upstanding from an inner surface of the upper wall of the chamber to define a plurality of air channels between the upper wall and the second section of the membrane when the second section of the membrane locates against the limiter.

20. The breast pump system according to claim 12, wherein the membrane wraps around the upper end of the lower part of the sidewall such that an outer edge of the membrane is located exterior to the chamber.

\* \* \* \* \*